(12) United States Patent
Fanger et al.

(10) Patent No.: US 7,935,123 B2
(45) Date of Patent: May 3, 2011

(54) DRILL GUIDE WITH ALIGNMENT FEATURE

(75) Inventors: Jonathan Fanger, Raynham, MA (US); Eric D. Kolb, Sandy Hook, CT (US)

(73) Assignee: Depuy Acromed, Inc., Raynham, MA (US)

( * ) Notice: Subject to any disclaimer, the term of this patent is extended or adjusted under 35 U.S.C. 154(b) by 1301 days.

(21) Appl. No.: 10/664,575

(22) Filed: Sep. 17, 2003

(65) Prior Publication Data
US 2004/0204716 A1 Oct. 14, 2004

Related U.S. Application Data

(63) Continuation-in-part of application No. 10/609,123, filed on Jun. 27, 2003, and a continuation-in-part of application No. 10/409,958, filed on Apr. 9, 2003, now Pat. No. 7,416,553.

(51) Int. Cl.
*A61B 17/58* (2006.01)
(52) U.S. Cl. .......................... 606/96; 606/86 B
(58) Field of Classification Search .............. 606/96–99, 606/104, 86 A, 86 B, 914–915, 60, 246; 269/47, 269/53, 100, 900, 289 R; 29/281.1
See application file for complete search history.

(56) References Cited

U.S. PATENT DOCUMENTS

| | | | |
|---|---|---|---|
| 1,920,821 A | 8/1933 | Wassernaar | |
| 2,466,023 A | 4/1949 | Griffin | |
| 2,486,303 A | 10/1949 | Longfellow | |
| 2,494,229 A | 1/1950 | Wollpert et al. | |
| 2,695,688 A | 11/1954 | Wollpert et al. | |
| 2,756,742 A | 7/1956 | Barton | |
| 3,244,170 A | 4/1966 | McElvenny | |
| 3,463,148 A | 8/1969 | Allgower et al. | |
| 3,552,389 A | 1/1971 | Allgower et al. | |
| 3,596,656 A | 8/1971 | Kaute et al. | |
| 3,626,471 A | 12/1971 | Florin | |
| 3,659,595 A | 5/1972 | Haboush | |
| 3,695,259 A | 10/1972 | Yost | |

(Continued)

FOREIGN PATENT DOCUMENTS
DE 4201043 1/1992
(Continued)

OTHER PUBLICATIONS

Product Literature, by Synthes Spine, "The Cervical Spine Locking Plate" CSLP, 2000.

(Continued)

*Primary Examiner* — Thomas C Barrett
*Assistant Examiner* — Larry E Waggle

(57) ABSTRACT

A guide device is provided for use with a spinal plate that has at least one pair of screw bores formed therein. The guide device generally includes an elongate shaft having a proximal end and a distal end. A guide member is coupled to the distal end of the elongate shaft and it includes at least one lumen extending therethrough, and at least one alignment element that is positioned distal of the guide member. Each alignment element(s) is adapted to interact with a spinal plate to position the guide member with respect to the spinal plate such that the each lumen in the guide member is aligned with a corresponding screw bore formed in the spinal plate. The guide member can then be used to guide a tool or implant through each lumen in the spinal plate and into bone.

20 Claims, 9 Drawing Sheets

U.S. PATENT DOCUMENTS

| | | | |
|---|---|---|---|
| 3,716,050 A | 2/1973 | Johnston | |
| 3,779,240 A | 12/1973 | Kondo et al. | |
| 3,824,995 A | 7/1974 | Getscher et al. | |
| 3,900,025 A | 8/1975 | Barnes, Jr. | |
| RE028,841 E | 6/1976 | Allgower et al. | |
| 4,119,092 A | 10/1978 | Gil et al. | |
| 4,187,841 A | 2/1980 | Knutson | |
| 4,219,015 A | 8/1980 | Steinemann et al. | |
| 4,224,699 A | 9/1980 | Weber et al. | |
| 4,257,411 A | 3/1981 | Cho | |
| 4,388,921 A * | 6/1983 | Sutter et al. | 606/71 |
| 4,408,601 A | 10/1983 | Wenk et al. | |
| 4,454,876 A | 6/1984 | Mears | |
| RE031,628 E | 7/1984 | Allgower et al. | |
| 4,493,317 A | 1/1985 | Klaue et al. | |
| 4,502,475 A | 3/1985 | Weigle et al. | |
| 4,503,848 A | 3/1985 | Caspar et al. | |
| 4,513,744 A | 4/1985 | Klaue et al. | |
| 4,524,765 A | 6/1985 | de Zbikowski et al. | |
| 4,541,424 A | 9/1985 | Grosse et al. | |
| 4,651,724 A | 3/1987 | Berentey et al. | |
| 4,686,972 A | 8/1987 | Kurland | |
| 4,733,657 A | 3/1988 | Kluger | |
| 4,744,353 A | 5/1988 | McFarland | |
| 4,773,402 A | 9/1988 | Asher et al. | |
| 4,800,874 A | 1/1989 | David et al. | |
| 4,838,252 A | 6/1989 | Klaue et al. | |
| 4,848,327 A | 7/1989 | Perdue | |
| 4,887,596 A | 12/1989 | Sherman | |
| 4,936,844 A | 6/1990 | Chandler et al. | |
| 4,957,495 A | 9/1990 | Kluger | |
| 5,002,544 A | 3/1991 | Klaue et al. | |
| 5,006,120 A | 4/1991 | Carter | |
| 5,041,113 A | 8/1991 | Biedermann et al. | |
| 5,041,114 A | 8/1991 | Chapman et al. | |
| 5,041,133 A | 8/1991 | Sayano et al. | |
| 5,052,373 A | 10/1991 | Michelson | |
| 5,053,036 A | 10/1991 | Perren et al. | |
| 5,059,194 A | 10/1991 | Michelson | |
| 5,067,477 A | 11/1991 | Santangelo | |
| 5,088,472 A | 2/1992 | Fakhrai | |
| 5,129,899 A | 7/1992 | Small et al. | |
| 5,129,903 A | 7/1992 | Luhr et al. | |
| 5,147,361 A | 9/1992 | Ojima et al. | |
| 5,151,103 A | 9/1992 | Tepic et al. | |
| 5,180,381 A | 1/1993 | Aust | |
| 5,234,290 A | 8/1993 | Collins | |
| 5,275,601 A | 1/1994 | Gogolewski et al. | |
| 5,303,694 A | 4/1994 | Mikhail | |
| 5,306,278 A | 4/1994 | Dahl et al. | |
| 5,318,567 A | 6/1994 | Vichard et al. | |
| 5,324,290 A | 6/1994 | Zdeblick et al. | |
| 5,324,295 A | 6/1994 | Shapiro | |
| 5,336,224 A | 8/1994 | Selman | |
| 5,342,295 A | 8/1994 | Imran | |
| 5,364,399 A | 11/1994 | Lowery et al. | |
| 5,365,921 A | 11/1994 | Bookwalter et al. | |
| 5,415,660 A | 5/1995 | Campbell et al. | |
| 5,423,826 A * | 6/1995 | Coates et al. | 606/96 |
| 5,439,463 A | 8/1995 | Lin | |
| 5,501,684 A | 3/1996 | Schlapfer et al. | |
| 5,520,690 A | 5/1996 | Errico et al. | |
| 5,531,746 A | 7/1996 | Errico et al. | |
| 5,531,751 A | 7/1996 | Schultheiss et al. | |
| 5,534,027 A | 7/1996 | Hodorek | |
| 5,549,612 A | 8/1996 | Yapp et al. | |
| 5,558,622 A | 9/1996 | Greenberg | |
| 5,578,034 A | 11/1996 | Estes | |
| 5,601,553 A | 2/1997 | Trebing et al. | |
| 5,603,713 A | 2/1997 | Aust | |
| 5,607,426 A | 3/1997 | Ralph et al. | |
| 5,607,428 A | 3/1997 | Lin | |
| 5,616,142 A | 4/1997 | Yuan et al. | |
| 5,616,144 A | 4/1997 | Yapp et al. | |
| 5,643,265 A | 7/1997 | Errico et al. | |
| 5,651,283 A | 7/1997 | Runciman et al. | |
| 5,669,915 A | 9/1997 | Caspar et al. | |
| 5,672,177 A | 9/1997 | Seldin | |
| 5,676,666 A * | 10/1997 | Oxland et al. | 606/61 |
| 5,713,904 A | 2/1998 | Errico et al. | |
| 5,735,853 A | 4/1998 | Olerud et al. | |
| 5,745,884 A * | 4/1998 | Carnegie et al. | 705/34 |
| 5,749,873 A | 5/1998 | Fairley et al. | |
| 5,749,884 A | 5/1998 | Benderev et al. | |
| 5,755,721 A | 5/1998 | Hearn | |
| 5,788,630 A | 8/1998 | Furnish | |
| 5,807,396 A | 9/1998 | Raveh | |
| 5,827,286 A | 10/1998 | Incavo et al. | |
| 5,836,950 A | 11/1998 | Hansson | |
| RE036,020 E | 12/1998 | Moore et al. | |
| 5,846,193 A | 12/1998 | Wright | |
| 5,851,207 A | 12/1998 | Cesarone | |
| 5,865,848 A | 2/1999 | Baker | |
| 5,876,402 A | 3/1999 | Errico et al. | |
| 5,885,286 A | 3/1999 | Sherman et al. | |
| 5,888,204 A | 3/1999 | Ralph et al. | |
| 5,904,683 A | 5/1999 | Pohndorf et al. | |
| 5,931,838 A | 8/1999 | Vito | |
| 5,951,558 A | 9/1999 | Fiz et al. | |
| 5,954,722 A | 9/1999 | Bono | |
| 5,964,762 A | 10/1999 | Biedermann et al. | |
| 5,964,763 A | 10/1999 | Incavo et al. | |
| 5,967,141 A | 10/1999 | Heinonen et al. | |
| 5,967,171 A | 10/1999 | Dwyer, Jr. | |
| 5,984,926 A | 11/1999 | Jones | |
| 6,006,581 A | 12/1999 | Holmes | |
| 6,017,345 A | 1/2000 | Richelsoph | |
| 6,030,389 A | 2/2000 | Wagner et al. | |
| 6,039,740 A | 3/2000 | Olerud et al. | |
| 6,063,090 A | 5/2000 | Schlapfer et al. | |
| 6,066,142 A | 5/2000 | Serbousek et al. | |
| 6,066,175 A | 5/2000 | Henderson et al. | |
| 6,106,527 A | 8/2000 | Wu et al. | |
| 6,113,602 A | 9/2000 | Sand | |
| 6,117,173 A | 9/2000 | Taddia et al. | |
| 6,132,432 A | 10/2000 | Richelsoph | |
| 6,139,550 A | 10/2000 | Michelson | |
| D433,506 S | 11/2000 | Asfora | |
| 6,143,012 A * | 11/2000 | Gausepohl | 606/185 |
| 6,152,927 A | 11/2000 | Farris et al. | |
| 6,159,244 A | 12/2000 | Suddaby | |
| 6,193,721 B1 * | 2/2001 | Michelson | 606/70 |
| 6,200,348 B1 | 3/2001 | Biedermann et al. | |
| 6,206,828 B1 | 3/2001 | Wright | |
| 6,206,881 B1 | 3/2001 | Frigg et al. | |
| 6,224,602 B1 | 5/2001 | Hayes | |
| 6,227,124 B1 | 5/2001 | Gaydos et al. | |
| 6,228,085 B1 | 5/2001 | Theken et al. | |
| 6,235,033 B1 | 5/2001 | Brace et al. | |
| 6,235,034 B1 | 5/2001 | Bray | |
| 6,241,731 B1 | 6/2001 | Fiz et al. | |
| 6,258,092 B1 | 7/2001 | Dall et al. | |
| 6,258,098 B1 | 7/2001 | Taylor et al. | |
| 6,261,291 B1 | 7/2001 | Talaber et al. | |
| 6,273,889 B1 | 8/2001 | Richelsoph | |
| 6,277,124 B1 | 8/2001 | Haag | |
| 6,293,949 B1 | 9/2001 | Justis et al. | |
| 6,306,136 B1 | 10/2001 | Baccelli | |
| 6,306,139 B1 * | 10/2001 | Fuentes | 606/70 |
| 6,309,393 B1 | 10/2001 | Tepic et al. | |
| 6,322,562 B1 | 11/2001 | Wolter et al. | |
| 6,328,738 B1 | 12/2001 | Suddaby | |
| 6,331,179 B1 | 12/2001 | Freid et al. | |
| 6,332,887 B1 | 12/2001 | Knox | |
| 6,340,363 B1 | 1/2002 | Bolger et al. | |
| 6,342,055 B1 | 1/2002 | Eisermann et al. | |
| 6,342,056 B1 | 1/2002 | Mac-Thiong et al. | |
| 6,342,057 B1 | 1/2002 | Brace et al. | |
| 6,379,364 B1 * | 4/2002 | Brace et al. | 606/96 |
| 6,402,756 B1 | 6/2002 | Ralph et al. | |
| 6,413,259 B1 | 7/2002 | Lyons et al. | |
| 6,416,518 B1 | 7/2002 | DeMayo | |
| 6,419,678 B1 | 7/2002 | Asfora | |
| 6,428,542 B1 | 8/2002 | Michelson | |
| 6,441,602 B1 | 8/2002 | Eckhardt et al. | |
| 6,447,512 B1 | 9/2002 | Landry et al. | |
| 6,454,769 B2 | 9/2002 | Wagner et al. | |

| | | |
|---|---|---|
| 6,503,250 B2 | 1/2003 | Paul |
| 6,511,484 B2 | 1/2003 | Torode et al. |
| 6,524,318 B1 | 2/2003 | Longhini et al. |
| 6,527,776 B1 | 3/2003 | Michelson |
| 6,533,786 B1 | 3/2003 | Needham et al. |
| 6,545,769 B2 | 4/2003 | Collard et al. |
| 6,565,571 B1 | 5/2003 | Jackowski |
| 6,575,975 B2 | 6/2003 | Brace et al. |
| 6,585,738 B1 | 7/2003 | Mangione et al. |
| 6,592,586 B1 | 7/2003 | Michelson |
| 6,595,993 B2 | 7/2003 | Donno et al. |
| 6,602,255 B1 | 8/2003 | Campbell et al. |
| 6,602,257 B1 | 8/2003 | Thramann |
| 6,620,163 B1 | 9/2003 | Michelson |
| 6,641,613 B2 | 11/2003 | Sennett |
| 6,652,525 B1 | 11/2003 | Assaker et al. |
| 6,656,181 B2 | 12/2003 | Dixon et al. |
| 6,663,562 B2 | 12/2003 | Chang |
| 6,669,700 B1 | 12/2003 | Farris et al. |
| 6,673,115 B2 | 1/2004 | Resch et al. |
| 6,679,883 B2 | 1/2004 | Hawkes et al. |
| 6,692,503 B2 * | 2/2004 | Foley et al. .................. 606/96 |
| 6,695,846 B2 | 2/2004 | Richelsoph et al. |
| 6,712,818 B1 | 3/2004 | Michelson |
| 6,755,833 B1 | 6/2004 | Paul et al. |
| 6,770,096 B2 | 8/2004 | Bolger et al. |
| 6,793,658 B2 | 9/2004 | LeHuec et al. |
| 6,796,986 B2 | 9/2004 | Duffner |
| 6,913,463 B2 | 7/2005 | Blacklock |
| 6,960,216 B2 * | 11/2005 | Kolb et al. .................. 606/96 |
| 7,011,665 B2 * | 3/2006 | Null et al. .................. 606/99 |
| 7,094,242 B2 * | 8/2006 | Ralph et al. .................. 606/96 |
| 7,147,599 B2 | 12/2006 | Phillips et al. |
| 7,278,997 B1 * | 10/2007 | Mueller et al. .............. 606/104 |
| 7,357,804 B2 | 4/2008 | Binder, Jr. et al. |
| 7,416,553 B2 | 8/2008 | Patel et al. |
| 7,488,327 B2 | 2/2009 | Rathbun et al. |
| 2001/0009971 A1 | 7/2001 | Sherts et al. |
| 2001/0021851 A1 | 9/2001 | Eberlein et al. |
| 2001/0037112 A1 | 11/2001 | Brace et al. |
| 2001/0047172 A1 | 11/2001 | Foley |
| 2002/0022843 A1 | 2/2002 | Michelson |
| 2002/0022847 A1 | 2/2002 | Ray et al. |
| 2002/0045897 A1 | 4/2002 | Dixon et al. |
| 2002/0045898 A1 | 4/2002 | Freid et al. |
| 2002/0049444 A1 | 4/2002 | Knox |
| 2002/0055741 A1 | 5/2002 | Schlapfer et al. |
| 2002/0058939 A1 | 5/2002 | Wagner et al. |
| 2002/0058940 A1 | 5/2002 | Frigg et al. |
| 2002/0082606 A1 | 6/2002 | Suddaby |
| 2002/0143336 A1 | 10/2002 | Hearn |
| 2002/0147450 A1 | 10/2002 | LeHuec et al. |
| 2002/0151899 A1 | 10/2002 | Bailey et al. |
| 2002/0156474 A1 | 10/2002 | Wack et al. |
| 2002/0183754 A1 | 12/2002 | Michelson |
| 2002/0183757 A1 | 12/2002 | Michelson |
| 2002/0188296 A1 | 12/2002 | Michelson |
| 2002/0198533 A1 | 12/2002 | Geisler et al. |
| 2003/0023242 A1 | 1/2003 | Harrington |
| 2003/0040749 A1 | 2/2003 | Grabowski et al. |
| 2003/0045880 A1 | 3/2003 | Michelson |
| 2003/0060828 A1 | 3/2003 | Michelson |
| 2003/0065251 A1 | 4/2003 | Feng et al. |
| 2003/0083658 A1 | 5/2003 | Hawkes et al. |
| 2003/0135213 A1 | 7/2003 | LeHuec et al. |
| 2003/0181912 A1 | 9/2003 | Michelson |
| 2003/0187436 A1 | 10/2003 | Bolger et al. |
| 2003/0187440 A1 | 10/2003 | Richelsoph et al. |
| 2003/0187442 A1 | 10/2003 | Richelsoph et al. |
| 2003/0187454 A1 * | 10/2003 | Gill et al. .................. 606/99 |
| 2003/0208204 A1 | 11/2003 | Bailey et al. |
| 2003/0229348 A1 | 12/2003 | Sevrain |
| 2003/0233098 A1 | 12/2003 | Markworth |
| 2004/0015169 A1 | 1/2004 | Gause |
| 2004/0015174 A1 | 1/2004 | Null |
| 2004/0019353 A1 * | 1/2004 | Freid et al. .................. 606/69 |
| 2004/0034352 A1 | 2/2004 | Needham et al. |
| 2004/0034354 A1 | 2/2004 | Paul |
| 2004/0087951 A1 | 5/2004 | Khalili |
| 2004/0092947 A1 * | 5/2004 | Foley .................. 606/96 |
| 2004/0097935 A1 | 5/2004 | Richelsoph et al. |
| 2004/0133205 A1 | 7/2004 | Thramann et al. |
| 2004/0204716 A1 | 10/2004 | Fanger et al. |
| 2005/0021040 A1 | 1/2005 | Bertagnoli |

FOREIGN PATENT DOCUMENTS

| | | |
|---|---|---|
| EP | 0897697 | 2/1999 |
| FR | 2827150 | 1/2003 |
| WO | 9632071 | 10/1996 |
| WO | WO-0022999 | 4/2000 |
| WO | 0064359 | 11/2000 |
| WO | 02085226 | 10/2002 |
| WO | WO-03/007826 | 1/2003 |
| WO | WO-03/024344 | 3/2003 |
| WO | 03063714 | 8/2003 |

OTHER PUBLICATIONS

Cervi-Lok Surgical Technique Manual (pp. 1-19), 1995 Spinetech Inc., L1015 Revision B.

* cited by examiner

*Fig. 8A*
*Fig. 8B*
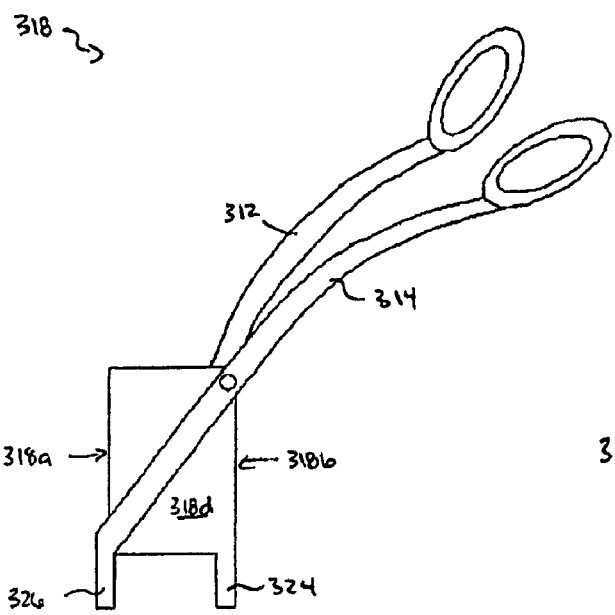
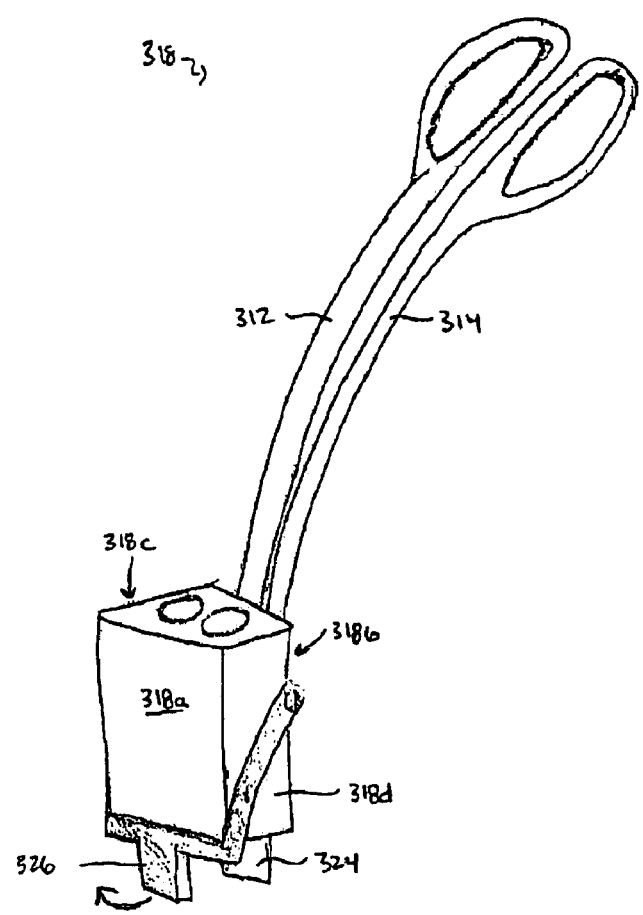

DRILL GUIDE WITH ALIGNMENT FEATURE

CROSS-REFERENCE TO RELATED APPLICATIONS

This application is a continuation-in-part of U.S. patent application Ser. No. 10/409,958 now U.S. Pat. No. 7,416,553, filed on Apr. 9, 2003 and entitled "Drill Guide and Plate Inserter," and U.S. patent application Ser. No. 10/609,123, filed on Jun. 27, 2003 and entitled "Tissue Retractor and Drill Guide," which are expressly incorporated by reference herein.

FIELD OF THE INVENTION

The present invention relates to devices for assisting in spinal surgery, and more particularly to a drill guide for introducing spinal tools and devices.

BACKGROUND OF THE INVENTION

Advancing age, as well as injury, can lead to changes in the bones, discs, joints, and ligaments of the spine, producing pain from nerve root compression. Under certain circumstances, alleviation of pain can be provided by performing a spinal fusion. This is a procedure that involves joining two or more adjacent vertebrae with a bone fixation device so that they no longer are able to move relative to each other. For a number of known reasons, bone fixation devices are useful for promoting proper healing of injured or damaged vertebral bone segments caused by trauma, tumor growth, or degenerative disc disease. The external fixation devices immobilize the injured bone segments to ensure the proper growth of new tissue between the damaged segments. These types of external bone fixation devices often include internal bracing and instrumentation to stabilize the spinal column to facilitate the efficient healing of the damaged area without deformity or instability, while minimizing any immobilization and post-operative care of the patient.

One such device is a bone fixation plate that is used to immobilize adjacent skeletal parts such as bones. Typically, the fixation plate is a rigid metal or polymeric plate that is positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in a proper position and to bridge a weakened or diseased area, such as when a disc, vertebral body or fragment has been removed.

Such fixation plates have been used to immobilize a variety of bones, including vertebral bodies of the spine. These bone plate systems usually include a rigid spinal plate having a plurality of screw openings. The openings are either holes or slots for screw placement. The spinal plate is placed against the damaged vertebral bodies and bone screws are used to secure the spinal plate to the spine and optionally to a prosthetic implant or bone graft positioned between the adjacent vertebrae. Implantation of the spinal plate, however, can be difficult. Each spinal plate must be properly aligned with the vertebral bodies, and holes for receiving the bone screws must be drilled into the vertebrae at precise angles. It is often necessary to use the spinal plate as a drill guide for drilling and tapping the bone in preparation for receiving the bone screws. Such a procedure can be difficult, however, as the surgeon is required to securely and rigidly hold the spinal plate against the vertebrae, obtain proper alignment, drill, tap, and finally set the bone screws.

Accordingly, there remains a need for an improved guide device that can be used to facilitate implantation of a spinal plate.

SUMMARY OF THE INVENTION

The present invention provides a guide device for use with a spinal plate that has at least one pair of screw bores formed therein. The guide device generally includes an elongate shaft having a proximal end and a distal end. A guide member is coupled to the distal end of the elongate shaft and it includes at least one lumen extending therethrough, and at least one alignment element that is positioned distal of the guide member. Each alignment element(s) is adapted to interact with a spinal plate to position the guide member with respect to the spinal plate such that the each lumen in the guide member is aligned with a corresponding screw bore formed in the spinal plate. The guide member can then be used to guide a tool or implant through each lumen in the spinal plate and into bone.

The alignment element(s) can have a variety of configurations, and in one embodiment each alignment element is a tab that extends distally from the guide member. Each tab is preferably adapted to non-fixedly interact with a spinal plate to align the guide member with the spinal plate. In an exemplary embodiment, the guide member includes first and second opposed alignment tabs that extend from opposed outer edges of the guide member either at positions that are substantially between the first and second lumens, or such that the first and second lumens are positioned between the first and second alignment tabs. In an alternative embodiment, opposed first and second tabs can extend distally from the guide member, and they can be movable between an open position, and a closed position wherein the tabs are adapted to engage opposed edges of a spinal plate. The device can also optionally or alternatively include at least one protrusion that extends distally from the guide member and that is adapted to be disposed within a corresponding bore formed in the spinal plate. In another embodiment, the alignment tab can be adapted to be disposed within a corresponding slot formed in a spinal plate, and/or the tab(s) can be adapted to prevent rotation between the guide member and a spinal plate when the guide member is coupled to the spinal plate.

The guide member of the guide device can also have a variety of configurations, and in one embodiment it can have a substantially rectangular, elongate shape with first and second lumens extending therethrough. The guide member can include opposed transverse sides which preferably have a width that is less than a width of opposed superior and inferior sides. In this configuration, the guide device preferably includes a first alignment tab that extends distally from the superior side of the guide member and a second alignment tab that extends distally from the inferior side of the guide member. The tab(s) can be configured to interact with a graft window formed in a spinal plate. Alternatively, the guide member can include first and second alignment tabs that extend distally from opposed transverse sides of the guide member. In another embodiment, the guide member can have a first barrel with a lumen extending therethrough, and a second barrel with a lumen extending therethrough. The first and second barrels can be positioned at an angle with respect to one another.

In yet another embodiment of the present invention, the alignment element(s) can be formed on a support member that is coupled to the distal end of the elongate shaft, and the alignment element(s) can be adapted to removably engage a spinal plate. The guide member is preferably slidably movable along the support member such that a position of the guide member with respect to a spinal plate engaged by the support member is adjustable. The device can also include an engagement mechanism that is formed on a distal end of the elongate shaft and that is adapted to releasably engage the support member such that the position of the guide member can be temporarily fixed. A trigger mechanism can be formed on the proximal end of the elongate shaft and coupled to the engagement mechanism for moving the engagement mechanism between an engaged position, wherein the guide member is fixed at a desired position, and a released position, wherein the guide member is slidably movable along the support member. In an exemplary embodiment, the support member is arch-shaped and each alignment element(s) is in the form of a substantially concave groove that is formed on an inner surface of the support member.

The guide member of the present invention can optionally be provided as part of a spinal fixation kit that includes a spinal plate having at least one screw bore formed therein for receiving a fastening element that is effective to mate the spinal plate to at least one vertebrae. The spinal plate can also include at least one graft window formed therein that is adjacent to at least one pair of opposed screw bores formed in the spinal plate.

BRIEF DESCRIPTION OF THE DRAWINGS

FIG. 8A is a side view illustration of yet another embodiment of a surgical drill guide device in accordance with the present invention;

FIG. 8B is a perspective view illustration of the surgical drill guide device of FIG. 8A;

DETAILED DESCRIPTION OF THE INVENTION

The present invention provides a drill guide device that is useful during spinal surgery to facilitate implantation of a spinal implant, such as a spinal plate. In general, the device includes an elongate shaft having a proximal end and a distal end that is coupled to a guide member. The guide member includes at least one, and preferably two lumens extending therethrough for receiving a tool. At least one alignment element is positioned distal of the guide member, and it is adapted to interact with a spinal plate to position the guide member with respect to the spinal plate such that each lumen in the guide member is aligned with a corresponding screw bore formed in the spinal plate. In one embodiment, the alignment element(s) does not rigidly attach to the spinal plate, thus allowing the guide member to advantageously be quickly and easily positioned and aligned with the spinal plate. In other embodiments, the configuration of the alignment element(s) allows the guide member to have a relatively small profile, unlike some prior art devices. Moreover, the guide member can include one or more alignment tabs, at least one of which can interact with a graft window formed in a spinal plate. Since a graft window is an internal component of a spinal plate, the guide member can be positioned over and aligned with the spinal plate without impinging on any adjacent soft tissues that may be located at the lateral edges of the spinal plate.

A person skilled in the art will appreciate that, while the device 10 is described for use in connection with a spinal plate, the drill guide device can be used with a variety of implants for a variety of medical procedures.

Figure 1:
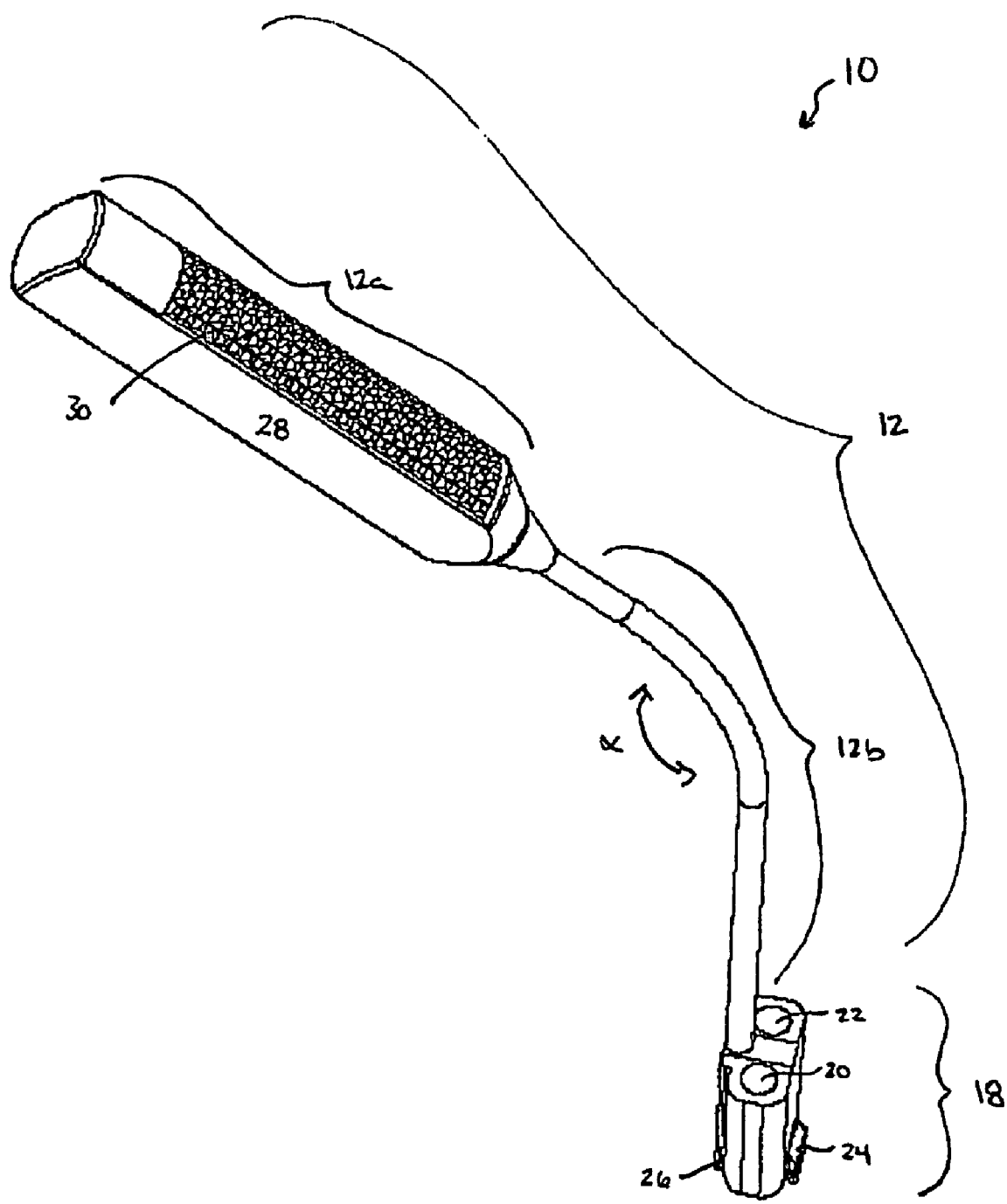
FIG. 1 is a perspective view of one embodiment of a drill guide device in accordance with the present invention.

FIG. 1 illustrates one embodiment of a guide device 10 in accordance with the present invention. As shown, the device 10 generally includes an elongate shaft 12 having a proximal portion 12a, and a distal portion 12b that is coupled to a guide member 18. The guide member 18 includes first and second lumens 20, 22 formed therein and extending therethrough. The lumens 20, 22 are adapted to be aligned with corresponding screw bores formed in a spinal plate when the guide member 18 is coupled to the spinal plate. Features for facilitating alignment of the guide member 18 with a spinal plate will be discussed in more detail below.

The elongate shaft 12 of device 10 can have a variety of configurations, shapes and sizes, but in an exemplary embodiment, the proximal portion 12a is adapted to extend out of a patient's body, while the distal portion 12b is coupled to the guide member 18, which can be inserted into a surgical incision within in the patient's body. The distal end 12b can optionally be adapted to retract tissue, as is described in U.S. patent application Ser. No. 10/609,123, from which this application claims priority and which is incorporated herein by reference in its entirety. The proximal and distal portions 12a, 12b can be fixedly attached to, removably mated to, or integrally formed with one another, but preferably a portion of the shaft 12 is disposed at an angle α such that the proximal portion 12a is offset from the guide member 18 to facilitate visual and physical access to the surgical site. While the angle α in the shaft 12 can vary, in an exemplary embodiment, the angle α is in the range of about 110° to 160°, and more preferably it is in the range of about 125° to 145°. While only a single angle is shown, a person skilled in the art will appreciate that the elongate member 12 can include two or more bends to facilitate visual access to the surgical site and/or to facilitate positioning of the device 10 in the patient's body. Moreover, the proximal portion 12a can optionally be adjustably movable with respect to the distal portion 12b to allow the surgeon to adjust the angle and/or position of the proximal portion 12a with respect to the distal portion 12b.

The proximal portion 12a of elongate member 12 can have a variety of configurations, but it preferably includes a handle 28 formed thereon or mated thereto. The handle 28 can have virtually any shape and size, and it can optionally include a gripping surface 30, such as a knurled surface, ridges, or grooves, to further facilitate grasping of the device 10. In an alternative embodiment, or in addition to the handle 28, the proximal portion 12a of the elongate member 12 can include a clamp member (not shown) formed thereon or mated thereto that is effective to mate the device 10 to a surgical retractor, such as, for example a Bookwalter retractor. Alternatively, the surgical retractor can contain a post or surface for attaching to a Bookwalter retractor having a clamp. A person skilled in the art will appreciate that a variety of clamp members and/or other mating techniques can be used to mate the device 10 to a retractor or other type of support member.

The distal portion 12b of the elongate member 12 can also have a variety of shapes and sizes, but it should be adapted to couple to the guide member 18. In an exemplary embodiment, the distal portion 12b is fixedly attached to or integrally formed with the guide member 18 at a location that is substantially between, but offset from the center axis of the first and second lumens 20, 22 in the guide member 18. This offset design will provide better visual and physical access to the guide member 18, since the elongate shaft 12 extends from a side of the guide member 18. A person skilled in the art will appreciate that the distal portion 12b of the elongate member 12 can be removably mated to the guide member 18, and/or it can be mated to virtually any portion of the guide member 18.

Figure 2A:
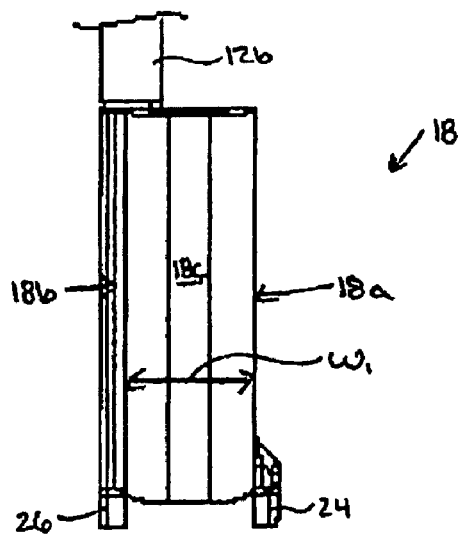
FIG. 2A is an enlarged side view of the guide member on the drill guide device shown in FIG. 1.
Figure 2B:
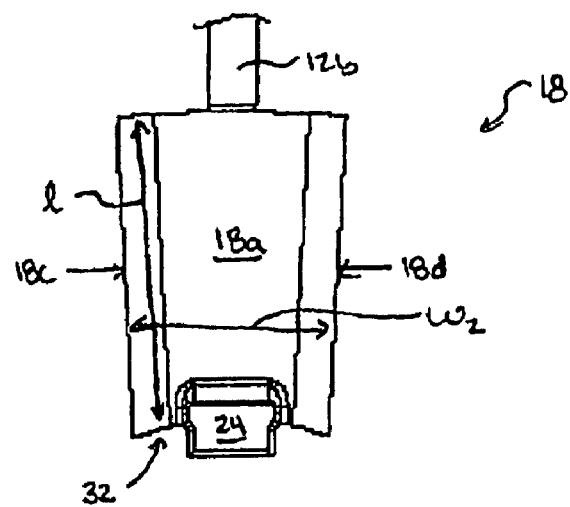
FIG. 2B is an enlarged front view of the guide member on the drill guide device shown in FIG. 1.

The guide member 18, which is shown in more detail in FIGS. 2A and 2B, can also have a variety of configurations, shapes, and sizes, but in an exemplary embodiment the guide member 18 preferably has a substantially rectangular, elongate shape. For reference purposes, each side of the guide member 18 will be referred to in accordance with its location when the guide member 18 is in use. Thus, the guide member 18 includes opposed superior and inferior sides 18a, 18b, and opposed first and second transverse sides 18c, 18d that extend between the opposed superior and inferior sides 18a, 18b. The transverse sides 18c, 18d preferably have a width $w_1$ that is less than a width $w_2$ of the superior and inferior sides 18a, 18b. The guide member 18 further includes at least one lumen formed therein for receiving a tool, such as an awl, a drill bit, a fastener, or a driver device. In use, a distal end surface 32 of the guide member 18 is adapted to rest against a spinal plate. In an exemplary embodiment, the distal end surface 32 of the guide member 18 has a shape that is adapted to match the contour (in the transverse direction) of a spinal plate. As shown in FIG. 2B, for example, the distal end surface 32 of the guide member 18 can have a substantially concave shape that is adapted to rest against a spinal plate having a convex surface. The guide member 18 should, however, have a shape and size that results in the alignment of the lumens 20, 22 with corresponding bores formed in a spinal plate coupled to the device 10, as will be discussed below.

As is further shown in FIGS. 1-2B, the guide member 18 also includes first and second lumens 20, 22 formed therein. While the lumens 20, 22 are formed through a solid housing, the lumens 20, 22 can alternatively be formed through separate barrels, as shown in FIG. 5B. Moreover, each lumen 20, 22 in the guide member 18 can extend therethrough at a variety of angles, and the guide member 18 can be configured such that the length l of each lumen 20, 22 is adjustable. For example, the barrels can be extendable, or the guide member 18 can include one or more extension sleeves that mate to each lumen 20, 22. In another embodiment, the first and second barrels can be removable and/or they can have an adjustable angle. More particularly, a base plate (not shown) can extend between the distal end of two barrels to mate the barrels to one another. The base plate can include bores formed therein for removably or fixedly receiving the barrels. Removable barrels are particularly advantageous in that they allow barrels having different lengths to be selected based on the intended use.

In use, the guide member 18 is preferably adapted to interact with a spinal plate such that the lumens 20, 22 in the guide member 18 are aligned with corresponding bores formed in the spinal plate. Accordingly, in order to facilitate alignment of the guide member 18 with the spinal plate, the device 10 can also include one of more alignment elements. Each alignment element can have a variety of configurations, and it can be adapted to interact with various features on a spinal plate. Moreover, the alignment element(s) can be configured to non-rigidly or rigidly couple to the spinal plate, and/or the alignment element(s) can interact with the spinal plate to either prevent rotation or to allow some rotation of the guide member 18 with respect to the spinal plate.

As shown in FIGS. 1-2B, guide member 18 includes opposed first and second alignment tabs 24, 26 extending distally therefrom. The tabs 24, 26 are effective to interact with edges formed on a spinal plate to align the lumens 20, 22 in the guide member 18 with corresponding bores in the spinal plate. The shape, size, and position of each tab 24, 26 can vary, and they can be adapted to match the contour of particular portions of a spinal plate. In the illustrated embodiment, the tabs 24, 26 have a substantially rectangular shape and they are positioned on and they extend distally from the opposed superior and inferior surfaces 18a, 18b of the guide member 18 at a location that is substantially between the lumens 20, 22. As a result, one tab 24, 26 can be positioned against a superior or inferior edge of a spinal plate, and the other tab 24, 26 can be positioned on an edge of a graft window formed in the spinal plate, as will be discussed in more detail below. The location of the tabs on the superior and inferior surfaces 18a, 18b of the guide member 18 is particularly advantageous in that it prevents the tabs from impinging on any adjacent soft tissues that may be located at the lateral edges of the spinal plate when the guide member 18 is coupled to a spinal plate.

While the tabs 24, 26 preferably do not rigidly engage the spinal plate, they can provide a clearance fit therebetween to prevent rotation of the guide member 18 with respect to the spinal plate when the tabs 24, 26 are aligned therewith. This is advantageous in that the tabs 24, 26 allow the guide member 18 to be quickly and easily positioned against, and subsequently removed from, the spinal plate. In an alternative embodiment, however, the tabs 24, 26 can be configured to engage and/or fixedly interact with the spinal plate. By way of non-limiting example, the tabs can be formed from a compliant material that allows the tabs 24, 26 to flex to engage the spinal plate. In other embodiments, the tabs 24, 26 can be adapted to extend into corresponding slots formed in the spinal plate, and/or they can provide a snap-fit engagement with the spinal plate. For example, each tab 24, 26 can include a ridge formed thereon that is adapted to fit within a corresponding groove formed in an edge of the spinal plate or formed within a slot in the spinal plate. In this configuration, the tabs 24, 26 should be slightly flexible to allow the tabs to engage and disengage the spinal plate. Additional techniques for aligning the guide member 18 with a spinal plate will be discussed in more detail below.

Figure 3:
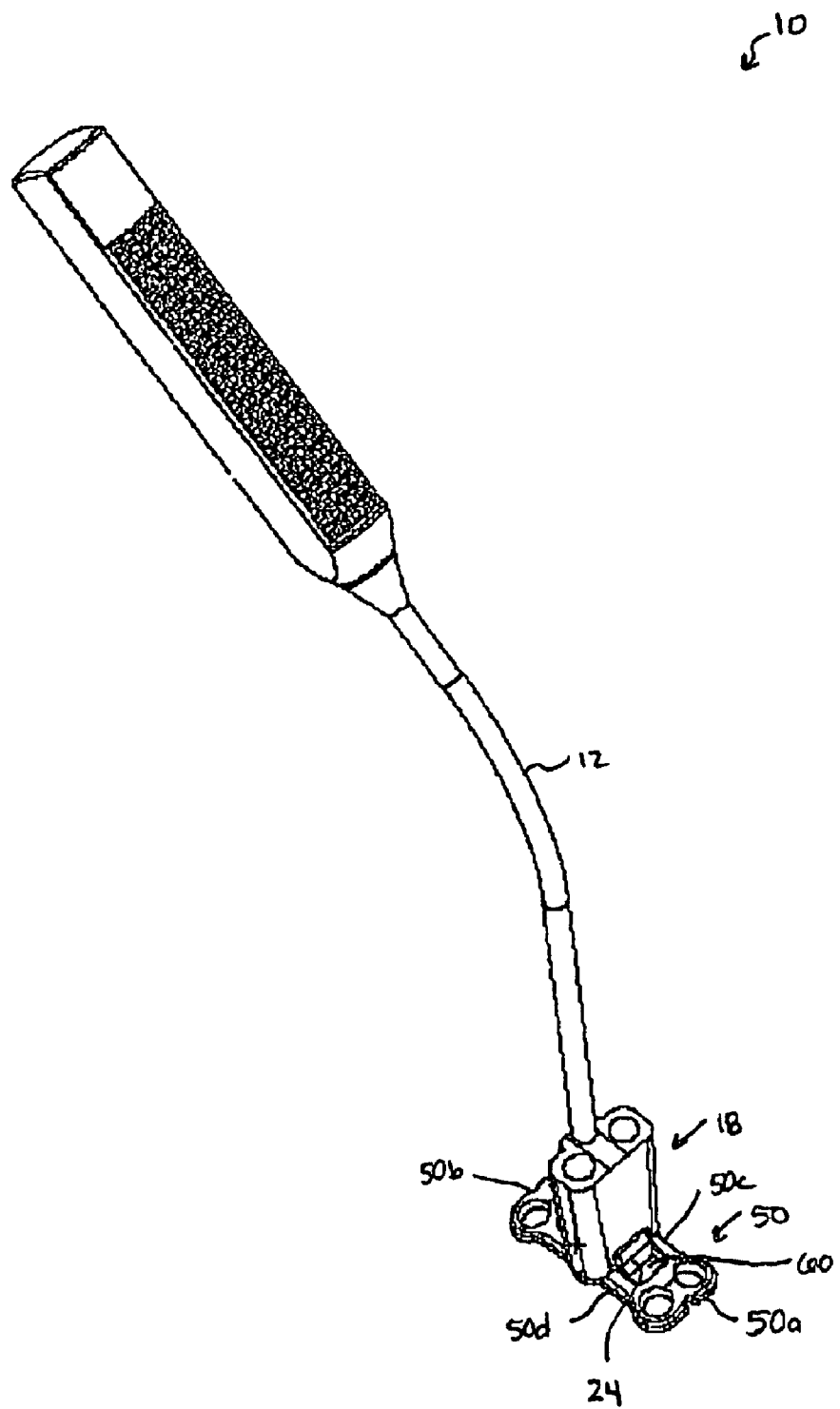
FIG. 3 is a perspective view of the drill guide device of FIG. 1 coupled to a pair of screw bores in a spinal plate.
Figure 4:
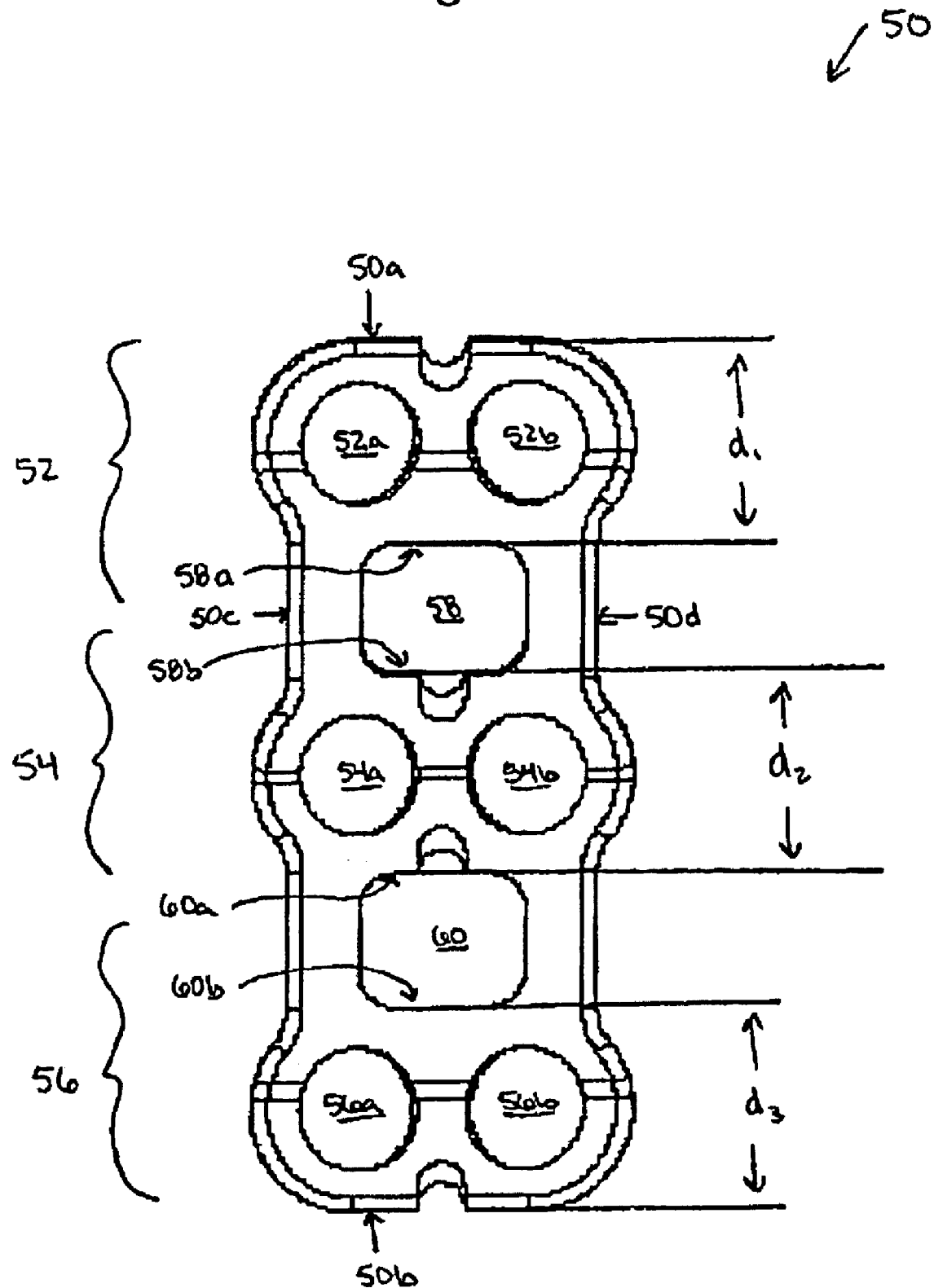
FIG. 4 is an enlarged perspective view of the spinal plate of FIG. 3.

FIG. 3 illustrates device 10 mated to an exemplary embodiment of a spinal plate 50, which is disclosed in more detail in a patent application filed concurrently herewith and entitled "Bone Fixation Plates." In general, the spinal plate 50, which is shown separately in FIG. 4, includes four outer edges: a superior edge 50a, an inferior edge 50b, and first and second opposed lateral sides 50c, 50d. As shown in FIG. 4, a first pair of screw bores 52a, 52b is formed in a superior portion 52 of the spinal plate 50, a second pair of screw bores 54a, 54b is formed a mid-portion 54 of the spinal plate 50, and a third pair of screw bores 56a, 56b is formed an inferior portion 56 of the spinal plate 50. The spinal plate 50 also includes a first graft window 58 formed therein between the first and second pair of screw bores 52a, 52b, 54a, 54b, and a second graft window 60 formed therein between the second and third pair of screw bores 54a, 54b, 56a, 56b. The graft windows 58, 60 are configured such that the distance $d_1$ between the superior edge 50a of the spinal plate 50 and a superior edge 58a of the first graft window 58 is equal to the distance $d_2$ between an inferior edge 58b of the first graft window 58 and a superior edge 60a of the second graft window 60, which is equal to the distance $d_3$ between an inferior edge 60b of the second graft window 60 and the inferior edge 50b of the spinal plate 50. This allows the opposed alignment tabs 24, 26 on the guide member 18 to be aligned with any one of the three pairs of screw bores 52a, 52b, 54a, 54b, 56a, 56b formed in the spinal plate 50. By way of non-limiting example, FIG. 3 illustrates the guide member 18 aligned with the second pair of screw bores 54a, 54b formed in the mid-portion 54 of the spinal plate 50. As shown, tab 24 is positioned adjacent to superior edge 60a of the second graft window 60, and tab 26 (not shown) is positioned adjacent to the inferior edge 58b of the first graft window 58.

Figure 5A:
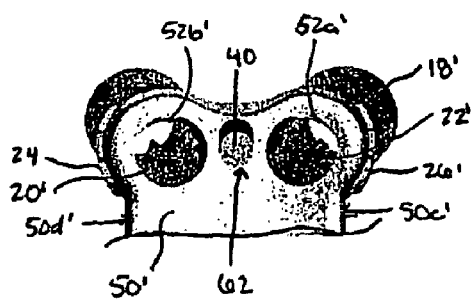
FIG. 5A is a bottom view of a portion of a spinal plate having another embodiment of a drill guide device coupled thereto in accordance with the present invention.
Figure 5B:
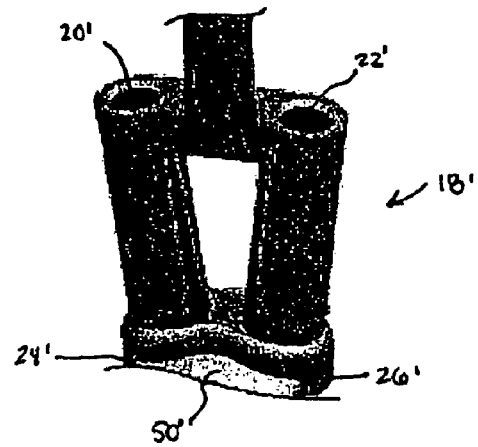
FIG. 5B is perspective side view of the drill guide device and spinal plate of FIG. 5A.

In an alternative embodiment, shown in FIGS. 5A-5B, the tabs 24', 26' on the guide member 18' can extend distally from the opposed transverse sides of the guide member 18' such that the lumens 20', 22' in the guide member 18' are positioned between the tabs 24', 26'. As a result, the tabs 24', 26' will align with the opposed lateral side edges 50c', 50d' of the spinal plate 50', as shown. In this embodiment, each tab 24', 26' can have a shape that conforms to a shape of the lateral edges 50c', 50d' of the spinal plate 50' adjacent to the screw bores 52a', 52b' formed in the spinal plate 50'. In particular, as shown in FIG. 5A, the tabs 24', 26' can have a concave shape, or at least a concave inner surface, that matches the convex shape of the spinal plate 50' along the lateral edges 50c', 50d' of the spinal plate 50 adjacent to the screw bores 52a', 52b' formed in the spinal plate 50'.

Still referring to FIG. 5A, in addition to, or as an alternative to, the tabs 24', 26', the guide member 18' can include a mating element, such as a protrusion or pin member 40, that extends from a distal surface thereof. The pin member 40 can be formed at any location on the guide member 18', but it is preferably at a location that is substantially between the first and second lumens 20', 22'. The pin member 40 is adapted to extend into a corresponding detent or bore 62 formed in the spinal plate 50'. The pin member 40 can optionally extend at an angle to further facilitate grasping the spinal plate 50'. In an exemplary embodiment, the pin member 40 is adapted to prevent rotation between the guide member 18' and the spinal plate 50' to provide stability to the connection. By way of non-limiting example, mating elements with non-symmetrical shapes, such as a pin with a non-circular cross section (e.g., rectangular, oval, triangular, irregular), a multi-pronged mating element, or a tongue-and-groove combination, can prevent or reduce the tendency of the device 10' to pivot with respect to the spinal plate 50'.

Figure 6:
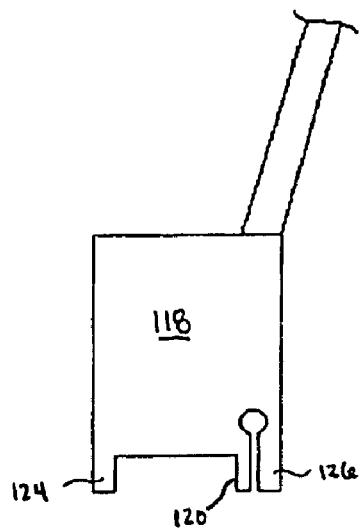
FIG. 6 is a side view illustration of portion of another embodiment of a surgical drill guide device in accordance with the present invention.
Figure 7:
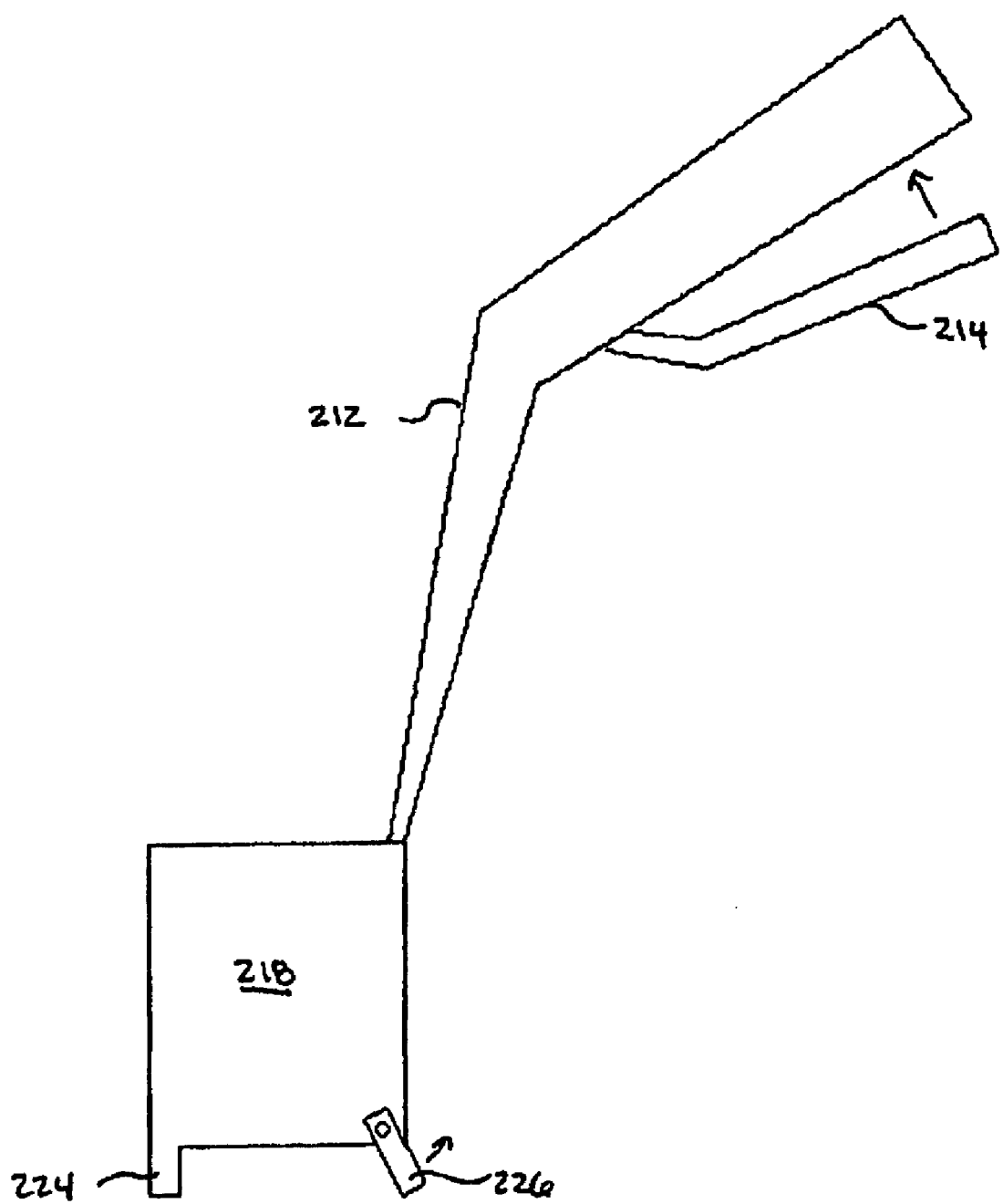
FIG. 7 is a side view illustration of a surgical drill guide device having a pivotable alignment mechanism in accordance with another embodiment the present invention.

A person skilled in the art will appreciate that a variety of other techniques can be used to align the guide member 18' with the spinal plate 50'. By way of non-limiting example, FIGS. 6-8 illustrate additional embodiments of alignment mechanisms for use with a drill guide device in accordance with the present invention. Each of the illustrated alignment mechanisms can be formed at a variety of locations on the guide member, and the guide member can include any number of alignment mechanisms having any of the illustrated configurations, as well as other configurations not shown or described herein.

FIG. 6 illustrates a guide member 118 having a fixed tab 124 and an opposed deflecting tab 120 that is adapted to provide a friction fit between a spinal plate and the guide member 118. The deflecting tab 120 can include a fixed tab portion 126 positioned adjacent thereto to prevent the deflecting tab 120 from accidentally breaking. In this embodiment, the tabs 120, 124, 126 can be formed on opposed transverse sides of the guide member, or alternatively they can be formed on superior and inferior sides of the guide member.

FIG. 7 illustrates another embodiment in which the guide member 218 includes a fixed tab 224 and a pivoting tab 226. The pivoting tab 226 can be coupled to a lever 214 that is formed on the handle of the shaft 212 for controlling the pivoting motion of the tab 226. A cable or similar element can extend between the lever 214 and the tab 226 for moving the tab 226 between open and closed positions. Again, like the embodiment illustrated in FIG. 6, the pivoting tab 226 and the fixed tab 224 can be formed on opposed transverse sides of the guide member, or alternatively they can be formed on superior and inferior sides of the guide member.

FIGS. 8A and 8B illustrate a similar embodiment of a guide member 318 having a pivoting alignment mechanism 326. In this embodiment, the shaft is in the form of a first handle member 312, which is preferably fixed with respect to the guide member 318, and a second handle member 314 that is pivotally coupled to the guide member 318. An alignment tab 326 is formed on the distal portion of the second handle member 314, such that movement of the second handle member 314 is effective to move the alignment tab 326 between open and closed positions. The tab 326, in combination with an opposed fixed tab 324, is effective to engage a spinal plate therebetween when the alignment tab 326 is in the closed position. While FIG. 8B illustrates tabs 324, 326 formed on superior and inferior sides 318a, 318b of the guide member 318, the tabs 324, 326 can optionally be formed on opposed transverse sides 318c, 318d of the guide member for engaging lateral edges of a spinal plate. A person skilled in the art will appreciate that a variety of other techniques can be employed for providing at least one pivotable alignment mechanism, and in general for aligning the guide member with a spinal plate.

The present invention also provides a guide device that includes a variable angle guide member. The guide device 400 is similar to guide device 10 described with respect to FIGS. 1-2B. However, the guide member 418 does not include alignment elements that are formed thereon and extending distally therefrom. While the alignment elements are positioned distal of the guide member 418, they are formed on a support member 500 that allows the angle of the guide member 418 to be adjusted.

Figure 9A:
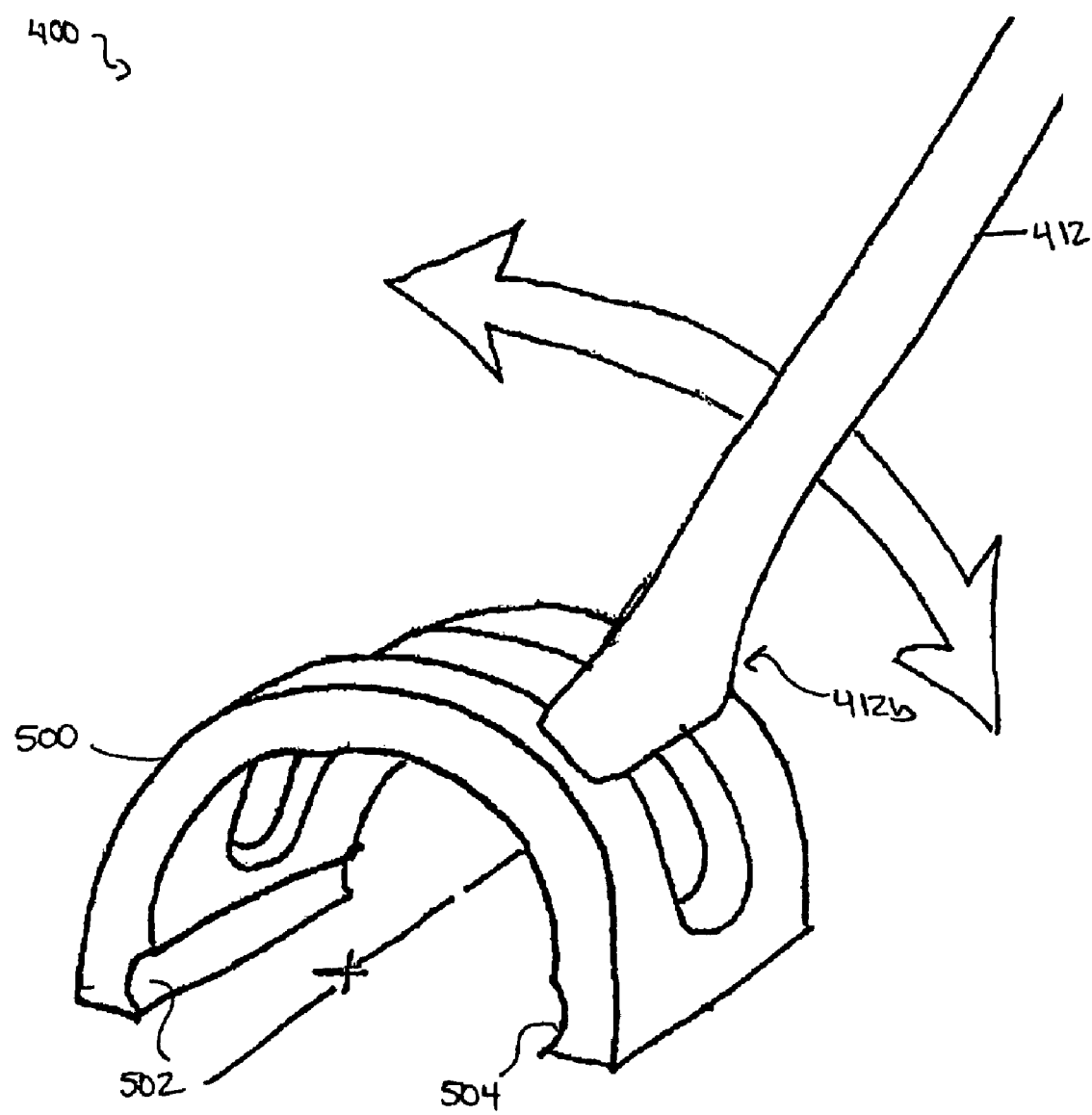
FIG. 9A is an enlarged perspective side view of a portion of a surgical drill guide device having support member coupled to an elongate shaft in accordance with another embodiment of the present invention.
Figure 9B:
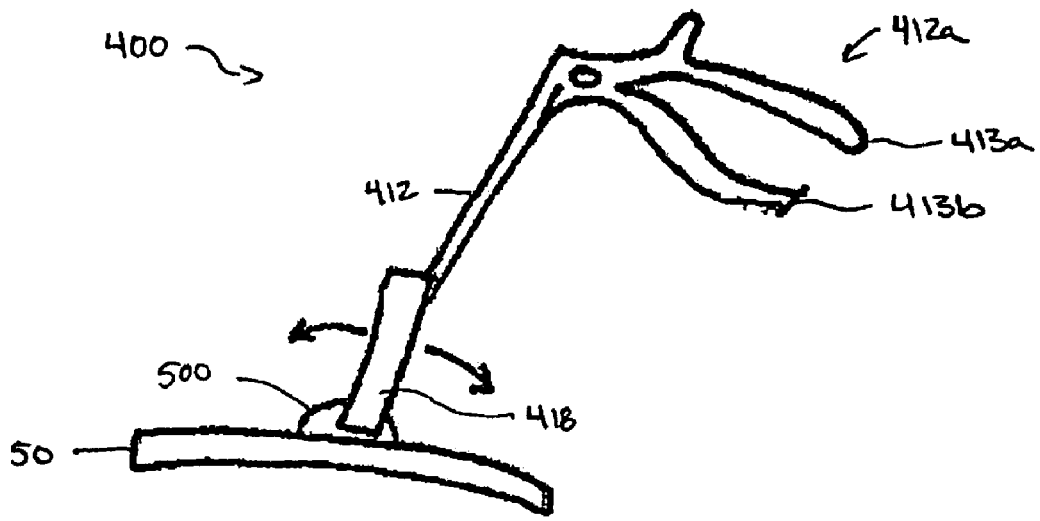
FIG. 9B is a perspective side view illustration of the surgical drill guide device of FIG. 9A coupled to a spinal plate.
Figure 9C:
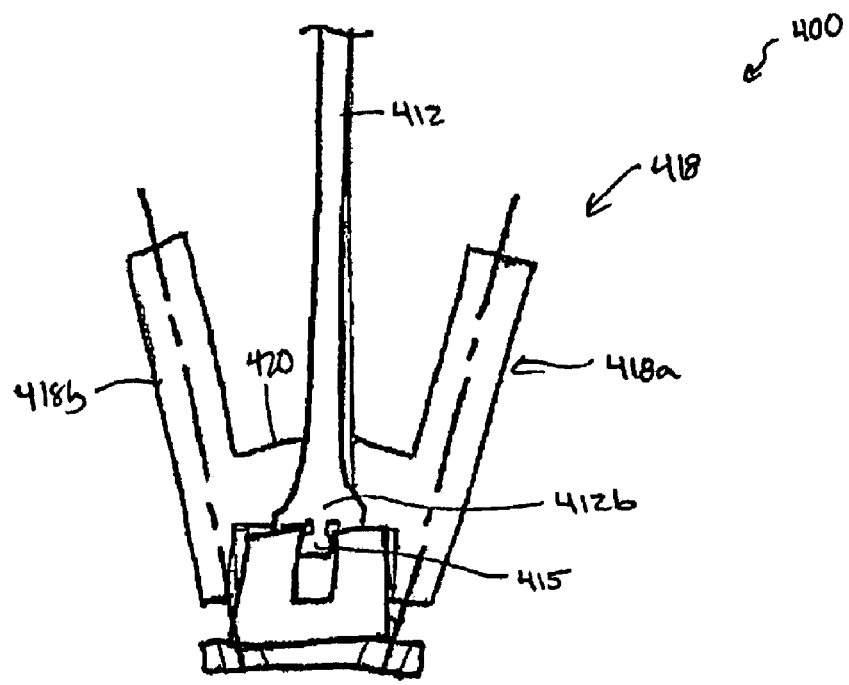
FIG. 9C is a perspective front view of a portion of the surgical drill guide device and spinal plate shown in FIG. 9B.

More particularly, as shown in FIGS. 9A-9C, the guide device 400 includes an elongate shaft 412 having a proximal, handle end 412a and a distal end 412b. The distal end 412b of the shaft 412 is slidably coupled to a support member 500 which is adapted to couple to a spinal plate, e.g., spinal plate 50. A variety of techniques can be used to mate the distal end 412b of the shaft 412 to the support member 500, but it should be adjustable between several fixation positions. In an exemplary embodiment, as shown, the proximal, handle end 412a of the shaft includes first and second handles 413a, 413b that are effective to control movement of the shaft 412 with respect to the support member 500. One or both handles 413a, 413b can be movable, but preferably handle 413a is fixed, and handle 413b is a trigger that is pivotable such that movement of trigger 413b is effective to engage and disengage the support member 500. An engagement mechanism, such as a brake 415, can be coupled to the distal end 412b of the shaft for engaging the support member 500. In use, actuation of the trigger 413b is preferably effective to release the brake 415 to allow the shaft 412 to be slidably movable with respect to the support member 500. When the shaft 412 is in the desired position, the trigger 413b can then be released to cause the brake 415 to re-engage the support member 500. The handles 413a, 413b can also include a ratchet mechanism (not shown) or other engagement mechanism for temporarily maintaining the position of the first and second handles 413a, 413b with respect to one another. A person skilled in the art will appreciate that a variety of other techniques can be used to effect and/or control movement of the shaft 412 and/or the guide member 418 with respect to the support member 500.

The distal end 412b, in addition to being coupled to a support member 500, is coupled to a guide member 418. As shown in FIG. 9C, the guide member 418 includes first and second barrels 418a, 418b having lumens extending therethrough for receiving a tool. Each barrel 418a, 418b is mated to one another and to the distal end 412b of the shaft 412 by a connection member 420. The connection member 420 allows the barrel 412a, 412b to be positioned on opposed sides of the support member 500, and to extend distal of the support member 500 such that the barrels 418a, 418b can be positioned adjacent to a spinal plate that is coupled to the support member 500.

An exemplary support member 500 is shown in more detail in FIG. 9A, and it can have a variety of configurations. The support member 500 is, however, preferably arch-shaped to allow the angle of the shaft 412, and thus the angle of the guide member 418, to be adjusted as desired. The support member 500 should also be adapted to engage opposed edges formed on a spinal plate, and in particular to engage a superior or inferior edge and/or an edge of a graft window. As shown in FIG. 9A, the support member 500 includes a substantially concave groove 502, 504 formed on an inner surface of each end of the support member 500. The opposed grooves 502, 504 are configured to fit around opposed edges of a spinal plate. A person skilled in the art will appreciate that a variety of other techniques, including those described herein, can be used to couple the support member 500 to a spinal plate. In an exemplary embodiment, however, the support member 500 should rigidly connect to or at least temporarily engage the spinal plate to prevent removal of the support member 500 during adjustment of the guide member 418.

The guide device of the present invention can also be provided as part of a spinal fixation kit that includes a spinal plate having at least one screw bore formed therein for receiving a fastening element that is effective to mate the spinal plate to at least one vertebrae. The spinal plate can also include at least one graft window formed therein that is adjacent to at least one pair of opposed screw bores formed in the spinal plate. The kit can include additional devices, tools, and/or implants, such as fastening devices, bone preparation devices, etc.

The guide devices of the present invention can be used to implant a variety of spinal plates, and once the spinal plate is properly positioned against the spine and the guide device is aligned with the spinal plate, a tool, such as a drill, awl, tap, or implant, can be passed through the each lumen in the guide member to form a borehole in the vertebrae and/or to insert a spinal implant into the vertebrae.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A guide device for use with a spinal plate having at least one pair of screw bores formed therein, the guide device comprising:
   an elongate shaft having a proximal end and a distal end;
   a guide member coupled to the distal end of the elongate shaft and including first and second lumens extending therethrough and immovable relative to one another, the first and second lumens having central axes that extend in a plane that is parallel to opposed superior and inferior surfaces of the guide member; and
   first and second opposed alignment tabs extending distally from the opposed superior and inferior surfaces of the guide member, the first and second opposed alignment tabs being adapted to interact with a spinal plate to position the guide member with respect to the spinal plate such that the first and second lumens in the guide member are aligned with a pair of corresponding screw bores formed in the spinal plate.

2. The guide device of claim 1, wherein the first and second opposed alignment tabs are adapted to non-fixedly interact with a spinal plate to align the guide member with the spinal plate.

3. The guide device of claim 1, further comprising at least one protrusion that extends distally from the guide member and that is adapted to be disposed within a corresponding bore formed in the spinal plate.

4. The guide device of claim 1, wherein the guide member has a substantially rectangular, elongate shape and the first and second lumens extend therethrough.

5. The guide device of claim 4, wherein the guide member includes opposed transverse surfaces extending between the opposed superior and inferior surfaces, the transverse surfaces having a width that is less than a width of the superior and inferior surfaces.

6. The guide device of claim 1, wherein a distal surface of the guide member has a shape that conforms to the shape of a spinal plate.

7. The guide device of claim 1, wherein the first and second lumens are positioned at an angle with respect to one another.

8. The guide device of claim 1, wherein the first and second alignment tabs are adapted to loosely interact with a spinal plate such that the guide member can pivot with respect to the spinal plate.

9. The guide device of claim 1, wherein the first and second lumens have an adjustable length.

10. The guide device of claim 1, wherein the proximal end on the elongate shaft is positioned at an angle with respect to a distal portion of the elongate shaft.

11. A guide device for use with a spinal plate having at least one screw bore formed therein, the guide device comprising:
    an elongate shaft having a proximal end and a distal end; and
    a guide member coupled to the distal end of the elongate shaft and including first and second lumens extending therethrough, the lumens having central axes that extend in a plane that is parallel to opposed superior and inferior surfaces of the guide member; and
    first and second opposed alignment tabs extending distally from the superior and inferior surfaces of the guide member, the first and second opposed alignment tabs being adapted to non-fixedly interact by abutting an edge of a spinal plate to position the guide member with respect to the spinal plate such that the first and second lumens in the guide member are aligned with at least one corresponding screw bore formed in the spinal plate.

12. A guide device for use with a spinal plate having at least one pair of screw bores formed therein, the guide device comprising:

an elongate shaft having a proximal end and a distal end;

a guide member coupled to the distal end of the elongate shaft and including first and second lumens extending therethrough in fixed relation to one another, the lumens having central axes that extend in a plane that is parallel to opposed superior and inferior surfaces of the guide member;

first and second alignment tabs extending distally from opposed superior and inferior surfaces of the guide member, the first and second alignment tabs being adapted to interact with a spinal plate to position the guide member with respect to the spinal plate such that the first and second lumens in the guide member are aligned with a pair of corresponding screw bores formed in the spinal plate; and at least one protrusion that is formed on and extends distally from the guide member and that is adapted to be disposed within a corresponding bore formed in the spinal plate.

13. The guide device of claim 12, wherein the at least one alignment tab comprises first and second alignment tabs extending distally from the superior and inferior surfaces.

14. The guide device of claim 12, wherein the at least one tab is adapted to non-fixedly interact with a spinal plate to align the guide member with the spinal plate.

15. The guide device of claim 12, wherein the at least one alignment tab is adapted to prevent rotation between the guide member and a spinal plate when the guide member is mated to a spinal plate.

16. The guide device of claim 15, wherein the at least one alignment tab comprises an oval protrusion that extends distally from a distal end of the guide member.

17. The guide device of claim 12, wherein a distal surface of the guide member has a shape that conforms to the shape of a spinal plate.

18. The guide device of claim 12, wherein the first and second lumens are positioned at an angle with respect to one another.

19. The guide device of claim 12, wherein the at least one alignment tab is adapted to loosely interact with a spinal plate such that the guide member can pivot with respect to the spinal plate.

20. The guide device of claim 12, wherein the proximal end on the elongate shaft is positioned at an angle with respect to a distal portion of the elongate shaft.

* * * * *

UNITED STATES PATENT AND TRADEMARK OFFICE
CERTIFICATE OF CORRECTION

| | | |
|---|---|---|
| PATENT NO. | : 7,935,123 B2 | Page 1 of 1 |
| APPLICATION NO. | : 10/664575 | |
| DATED | : May 3, 2011 | |
| INVENTOR(S) | : Jonathan Fanger | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1167 days.

Signed and Sealed this
Fourth Day of October, 2011

David J. Kappos
*Director of the United States Patent and Trademark Office*